United States Patent [19]
Arnold

[11] Patent Number: 5,880,117
[45] Date of Patent: Mar. 9, 1999

[54] USE OF 4-ANDROSTENEDIOL TO INCREASE TESTOSTERONE LEVELS IN HUMANS

[76] Inventor: Patrick Arnold, P.O. Box 160, Seymour, Ill. 61875

[21] Appl. No.: 114,114

[22] Filed: Jul. 13, 1998

[51] Int. Cl.⁶ .................................................... A61K 31/56
[52] U.S. Cl. ............................................................. 514/178
[58] Field of Search ................................................. 514/178

[56] References Cited

U.S. PATENT DOCUMENTS

| | | | |
|---|---|---|---|
| 5,387,583 | 2/1995 | Loria | 514/171 |
| 5,391,776 | 2/1995 | Ueno et al. | 552/507 |
| 5,578,588 | 11/1996 | Mattern et al. | |

*Primary Examiner*—Raymond Henley, III

[57] ABSTRACT

This invention relates to a method of administering the testosterone precursor 4-androstenediol as a means of increasing testosterone levels in humans.

4 Claims, 1 Drawing Sheet

Figure 1. Total Testosterone Responses
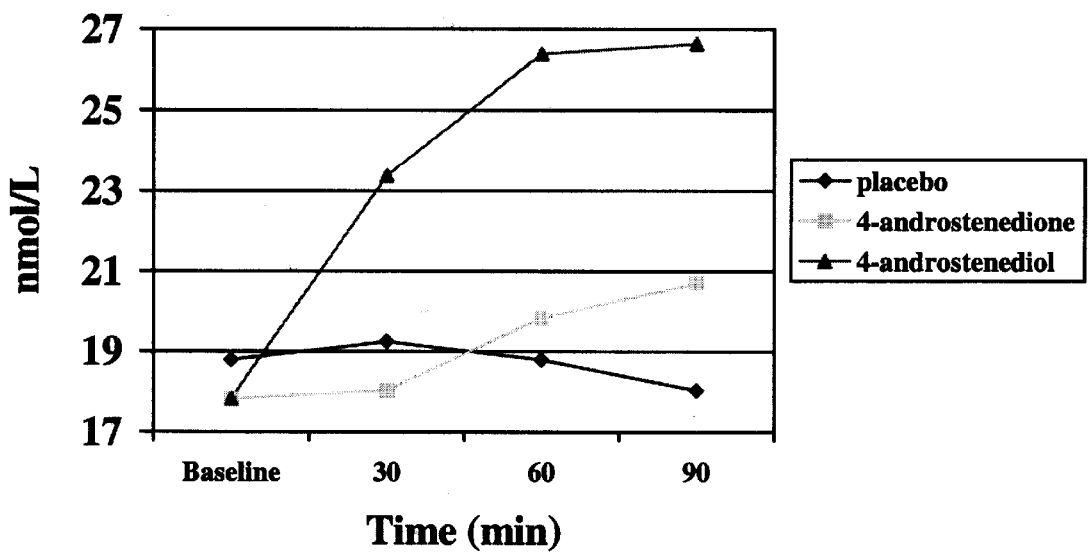
Figure 2. Free Testosterone Responses
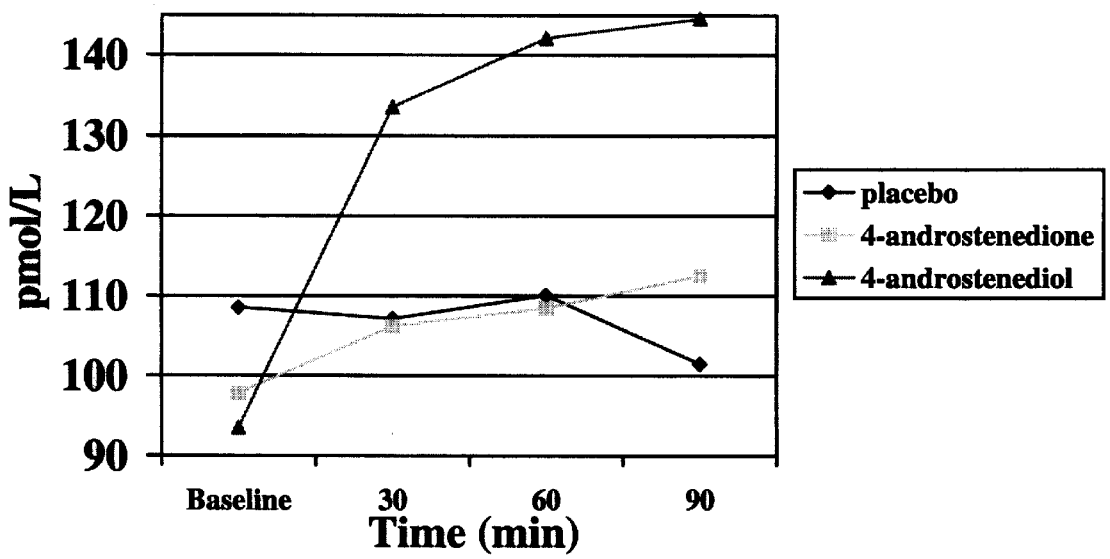

USE OF 4-ANDROSTENEDIOL TO INCREASE TESTOSTERONE LEVELS IN HUMANS

FIELD OF THE INVENTION

This invention relates to a method of administering the testosterone precursor 4-androstenediol as a means of increasing testosterone levels in humans. The steroid hormone testosterone is considered to be the male virilizing hormone. Its effects include maintenance of muscle and bone mass, sexual function, and psychological well being among others. As males grow older, especially after the age of 35, a slow decline in testosterone levels is observed which is accompanied by symptoms that have been associated with the condition known as "andropause". Symptoms of andropause include lethargy, depression, lack of sexual desire and function, and loss of muscle mass and strength.

DESCRIPTION OF THE PRIOR ART

There are several pharmaceutical methods to restore testosterone levels in humans with suboptimal levels. Many of these have disadvantages however. Testosterone esters in oil depot form have been used as injections for decades, however these injections can be inconvenient and often painful. These depot injections also result in inconsistent blood levels as a supraphysiological surge is seen soon after injection but by the time the next injection is due, the levels have often dropped down below standard physiological levels. This is in contrast with testosterone levels under normal conditions, which are quite stable within mild release pulses of approximately 90 minute duration. Supraphysiological surges that are seen with injectable preparations may increase the incidence of undesirable side effects (i.e. prostrate hypertrophy) as well as cause an amplified shutdown of the hypothalamic/pituitary testicular axis (HPTA).

Other pharmaceutical methods for androgen replacement therapy include synthetic oral androgen derivatives. These compounds (i.e. methyltestosterone and fluoxymesterone) are altered in the 17alpha position of the steroid molecule with an alkyl group. This alkyl group renders the steroid impervious to oxidation of the 17 beta hydroxyl group in the liver and therefore greatly improves its oral bioavailability compared to the non-alkylated steroids. However, this structural modification also has been associated with a greatly increased risk of hepatotoxicity. Therefore, these synthetic compounds are far from an ideal solution.

U.S. Pat. No. 5,578,588 to Mattern, et. al, discloses a method of increasing testosterone levels in humans by administering a testosterone precursor, namely androstenedione. Modes of administration discussed include peroral and intranasal. The pharmacokinetics of such an administration of a precursor is such that a peak in blood levels is seen at approximately 90 minutes with a subsequent decline to baseline within 3 hours. This fact permits one to more closely simulate the natural endogenous pulsatile release of testosterone through multiple daily dosing of a precursor. This should result in a more normal physiological response with a minimization of side effects and HPTA shutdown. Furthermore, since these precursors are natural steroid hormones found in the blood, and are not 17alpha alkylated compounds, the hepatoxicity is minimal.

DESCRIPTION OF THE INVENTION

In the course of our research, we have found that the blood testosterone level increases seen with the oral administration of androstenedione are far less and more variable than what is described in U.S. Pat. No. 5,578,588. It was therefore an object of this invention to discover another naturally occurring testosterone precursor that provided a greater blood testosterone level response than androstenedione but retained all the advantages of being a non-toxic, natural, and quickly metabolizable precursor. This would therefore permit oral administration at a reasonable dose providing a dependable therapeutic response.

The chemical term 4-androstenediol refers to two isomers: 4-androstene-3beta, 17betadiol and 4-androstene-3alpha, 17beta-diol. This invention concerns primarily the former isomer in the preferred embodiment.

4-androstenediol is a naturally occurring compound. It has been identified as a metabolite of testosterone in placental, uterine, testicular, adrenal, and hypothalamic/pituitary tissues. It acts as a very effective precursor to testosterone. 4-androstenediol converts to testosterone via the 3beta-hydroxysteroid dehydrogenase enzyme. F. Ungar, M. Gut, and R. Dorfman (*J Biol. Chem.*, 224, 191–200) found that after 4-androstenediol was incubated in liver tissue it metabolized very readily to testosterone. J. Blaquier, E. Forchielli, and R. Dorftnan (*Acta Endocrinologica*, 55, 697–704) also revealed that the in vitro conversion of tritiated 4-androstene-3beta, 17betadiol to testosterone in whole human blood was very efficient (15.76%) and was in fact considerably more efficient that tritiated androstenedione (5.61%).

After learning of the in-vitro efficacy of 4-androstenediol in regards to testosterone conversion, it was then the intention of the inventor to investigate whether 4-androstenediol would act as an effective in-vivo peroral testosterone precursor in humans. It was also the intention of the inventor to investigate whether or not 4-androstenediol would act as a superior peroral testosterone precursor to androstenedione.

A clinical study was therefore undertaken. Seven adult male subjects were used. Each subject was on separate occasions given an oral dose of 100 mg. placebo, 4-androstenediol, or androstenedione. Blood samples were collected at 0, 30, 60, and 90 minutes following ingestion and analyzed for total testosterone (TT) (see FIG. 1) and free testosterone (FT) (see FIG. 2) using enzyme-linked immunosorbent assay. Relative to placebo, androstenedione ingestion caused a 14.8% increase in total testosterone and a 10.9% increase in free testosterone at 90 minutes. 4-androstenediol ingestion caused greater responses, producing a 47.7% increase in total testosterone and a 42.5% increase in free testosterone at 90 minutes.

Oral 4-androstenediol can be given in daily doses of 25 mg. to 500 mg., preferably 100 to 300 mg. These daily doses can be divided into several subdoses with 3–5 being most preferable. In addition to peroral administration, 4-androstenediol can also be effectively administered by several other routes including transdermal, rectal (suppository), intranasal, and sublingual. A particularly advantageous method of sublingual administration involves complexing 4-androstenediol with beta-hydroxypropyl-beta-cyclodextrin which is then pressed into tablets. 4-androstenediol can also be effectively combined with androstenedione to produce a product that contains two precursors that convert to testosterone through two distinct enzyme systems.

The foregoing drawings and description of the invention are for illustration only. Modifications not included in the description which are obvious to those skilled in the art are intended to be included in the scope of the following claims.

DESCRIPTION OF THE DRAWINGS

The present invention will be more fully understood by reference to the following detailed description thereof when read in conjunction with the attached drawings, and wherein:

FIG. 1 is a graph of Total Testosterone level versus time in a clinical test of the invention.

FIG. 2 is a graph of Free Testosterone levels versus time in a clinical test of the invention.

I claim:

1. A method of increasing testosterone levels in humans by administration of 4-androstenediol.

2. The method of increasing testosterone levels in humans according to claim 1, wherein the mode of administration is peroral.

3. The method of increasing testosterone levels in humans according to claim 1, wherein a peroral daily dosage of 25 mg to 500 mg is taken.

4. The method of increasing testosterone levels in humans according to claim 1, wherein the 4-androstenediol is 4-androstene-3beta, 17betadiol.

* * * * *